US008063209B2

(12) United States Patent
Hilfinger et al.

(10) Patent No.: US 8,063,209 B2
(45) Date of Patent: *Nov. 22, 2011

(54) PHOSPHONYL ESTER CONJUGATES AS PRODRUGS

(75) Inventors: John Hilfinger, Ann Arbor, MI (US); Charles E. McKenna, Los Angeles, CA (US); Boris A. Kashemirov, Los Angeles, CA (US); Chi Pham, Los Angeles, CA (US); Kanokkarn Saejueng, Los Angeles, CA (US); Larryn Peterson, Los Angeles, CA (US)

(73) Assignees: TSRL, Inc., Los Angeles, CA (US); National Institute of Health (NIH), Washington, DC (US); The United States of America as represented by the Department of Health and Human Services (DHHS), Washington, DC (US); The United States of America as represented by the NIH Division of Extramural Inventions and Technology Resources (DEITR), Washington, DC (US)

( * ) Notice: Subject to any disclaimer, the term of this patent is extended or adjusted under 35 U.S.C. 154(b) by 104 days.

This patent is subject to a terminal disclaimer.

(21) Appl. No.: 12/404,764

(22) Filed: Mar. 16, 2009

(65) Prior Publication Data
US 2009/0270618 A1 Oct. 29, 2009

Related U.S. Application Data

(63) Continuation-in-part of application No. 11/174,812, filed on Jul. 1, 2005, now Pat. No. 7,511,051.

(60) Provisional application No. 61/036,747, filed on Mar. 14, 2005, provisional application No. 60/585,265, filed on Jul. 2, 2004.

(51) Int. Cl.
*C07F 9/02* (2006.01)
(52) U.S. Cl. ........................................................ 544/243
(58) Field of Classification Search .................. 544/243
See application file for complete search history.

(56) References Cited

U.S. PATENT DOCUMENTS
7,511,051 B2 * 3/2009 McKenna et al. ............. 514/274

OTHER PUBLICATIONS

Smith, M. B. Organic Synthesis, McGraw-Hill, Inc. 1994, Chapter 1.*
Liekens, et al., The Nucleotide Analog Cidofovir Suppresses Basic Fibroblast Growth Factor (FGF2) Expression and Signaling and Induces Apoptosis in FGF2-Overexpressing Endothelial Cells, Molecular Pharmacology, vol. 71, No. 3, 695-703 (2007).*

* cited by examiner

*Primary Examiner* — Andrew D Kosar
*Assistant Examiner* — Erich A Leeser
(74) *Attorney, Agent, or Firm* — Gifford, Krass, Sprinkle, Anderson & Citkowski, P.C.

(57) ABSTRACT

Cidofovir or foscarnet based compounds having an amino acid or dipeptide esters are provided as prodrugs.

5 Claims, 6 Drawing Sheets

18
D-Val-L-Ser-OiPr cHPMPC

19
D-Val-L-Ser-OiPr HPMPC

20
L-Val-L-Ser-OiPr cHPMPC

21
L-Val-L-Ser-OiPr HPMPC

22
L-Thr-OiPr cHPMPC

23
L-Thr-OMe cHPMPC

24

25

PHOSPHONYL ESTER CONJUGATES AS PRODRUGS

CROSS-REFERENCE TO RELATED APPLICATIONS

This application claims priority of U.S. Provisional Patent Application Ser. No. 61/036,747 filed Mar. 14, 2008; and is a continuation-in-part of U.S. patent application Ser. No. 11/174,812 filed Jul. 1, 2005, which claims priority of U.S. Provisional Patent Application Ser. No. 60/585,265 filed Jul. 2, 2004. These prior applications are incorporated herein by reference.

STATEMENT REGARDING FEDERALLY SPONSORED RESEARCH OR DEVELOPMENT

This invention was made with government support under Contract Nos. U01 AI061457 and R44 AI056864 awarded by the National Institutes of Health. The government has certain rights in the invention.

FIELD OF THE INVENTION

The present invention relates in general to prodrugs of phosphonyl compounds and in particular to esters thereof formed through condensation with an amino acid via the side chain hydroxyl group.

BACKGROUND OF THE INVENTION

The prodrug approach has been utilized widely since the late 1950s for increasing drug bioavailability as well as drug targeting after oral administration. A prodrug is a compound that undergoes transformation within the body before eliciting a therapeutic action. This strategy is based on chemically modifying an active substance by attaching pro-moieties to pharmacophores, which ideally should overcome the biochemical and physical barriers impeding drug transport of the parent substance. Limited oral bioavailability is usually attributed to poor membrane permeability, low aqueous solubility (in the gastrointestinal fluids), or extensive first-pass metabolism.

It was long thought that intestinal absorption of most drugs proceeded by passive diffusion, in which the lipid solubility of the drug molecule was the determining factor. However, many water-soluble compounds have been shown to move well across cell membranes utilizing specialized carrier-mediated transport mechanisms. These membrane transporters play a key role in determining exposure of cells or organisms to a variety of solutes including nutrients and cellular byproducts, as well as drug molecules. Efforts have been made to improve drug bioavailability by using different pro-moieties targeting various active transportation systems present in the small intestine. Examples of transportation systems include peptide transporters, organic cation transporters, organic anion transporters, glucose transporters, vitamin transporters, bile acid transporters, fatty acid transporters, phosphate transporters, monocarboxylic acid transporters, bicarbonate transporters, ABC transporters, nucleoside transporters and amino acid transporters, as described by H.-C. Shi et al, in: R. Mannhold, H. Kubinyi, G. Folkers, Eds., Methods and Principles in Medicinal Chemistry, Wiley-VCH, Weinheim, 2003; pp. 245 287, herein incorporated by reference. All of these transporters are mainly located in the brush border membrane with variable distribution along the gastrointestinal tract, and show diverse substrate specificities.

The peptide transporter-1 (PepT1) is known to play a critical role in the absorption of diverse drugs and prodrugs from the intestinal tract. PepT1 is located in the apical enterocytic membrane of the upper small intestine where it serves as a symporter, using an electrochemical proton gradient as its driving force. Human PepT1 (hPepT1) contains 708 amino acids oriented in 12 membrane-spanning domains. The hPepT1 carrier protein is stereoselective, with peptides that contain L-amino acid residues having higher affinity for binding and transport than peptides containing one or more D-amino acids.

Many pharmaceuticals are known to utilize the intestinal PepT1 to gain entry into the systematic circulation. Such pharmaceuticals include β-lactam antibiotics such as penicillins and cephalosporins, ACE-inhibitors, renin inhibitors, thrombin inhibitors, and the dipeptide-like anti-neoplastic drug bestatin, as well as prodrugs of ganciclovir L-Dopa and pamidronate. Valacyclovir is one example of a prodrug enhancing bioavailability (3- to 5-fold) compared to the parent drug (20%), acyclovir. The increased bioavailability is suggested to result from PepT1 mediated absorption and rapid hydrolysis to acyclovir. Since PepT1 is an important di/tri peptide transporter in human enterocytes, the transportation of hundreds of different possible dipeptides, thousands of possible tripeptides, and diverse drugs and prodrugs, implies broad substrate specificity for this transporter.

Cidofovir [(S)-1-(3-hydroxy-2-phosphonylmethoxypropyl)cytosine, HPMPC] has been approved in the clinic as a treatment for AIDS-related cytomegalovirus retinitis. Cidofovir is known for its broad-spectrum activity against virtually all DNA viruses. It has been shown to have therapeutic potential not only against cytomegalovirus, but also against other herpes viruses such as herpes simplex virus (HSV), varcella-zoster virus (VZV), Epstein-Barr virus (EBV) and human herpes virus types 6, 7, and 8. It also has anti-viral activity against adenoviruses, papovaviruses such as papillomavirus and polyomavirus, pox viruses such as variola virus (the etiological agent for small pox) and other orthopox viruses such as monkeypox virus, hepadnaviruses such as hepatitis B virus, and iridiovirus.

The basic structure of cidofovir is shown in formula (I).

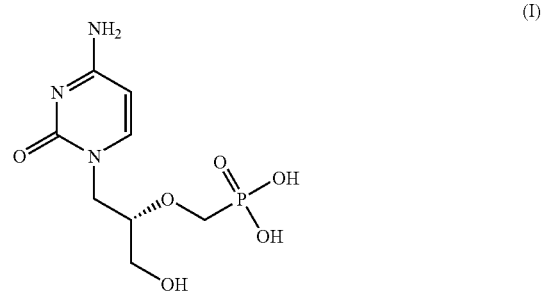

(I)

There is also a cyclic form of cidofovir. Cyclic cidofovir has a six-membered ring having two oxygen atoms, as shown in formula (II).

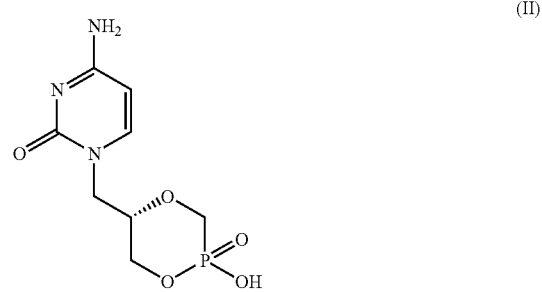

(II)

The potential use of variola virus and monkeypox virus as bioterrorism weapons has stimulated efforts to develop new drugs for treatment of smallpox and other pox infections. Cidofovir has been approved for use in the treatment of smallpox. Although, cidofovir is a very active agent against orthopoxviruses in vitro and in animal model infections; it does not show activity when administered orally due to lack of bioavailability via the oral route. Thus, cidofovir must be given systemically by injection or intravenously. Accordingly, there is a need to develop cidofovir-based drugs with enhanced oral bioavailability.

SUMMARY OF THE INVENTION

An inventive prodrug compound also has the formula:

$$\text{(V)}$$

where Nt is $Q$ is O or S; $R^3$ is —$(CH_2)_n$—, —$CHCH_3(CH_2)_n$—, and —$(C_6H_4)(CH_2)_n$; $R^4$ is O-isopropyl, O-isobutyl, O-tert-butyl or O-2-tert-pentyl, —O—$(CH_2)_n$—$C_6R_5^{10}$, —O—$(CH_2)_n$—CH—$(C_6R_5^{10})_2$, —O—$(CH_2)_nC(C_6R_5^{10})_3$, and —O—$C_5N'R_5^{10}$; n is independently in each occurrence an integer between 0 and 12; $R^{10}$ is independently in each occurrence H, F, Cl, Br, $C_1$-$C_4$ alkyl, $C_0$-$C_4$ primary amine, $C_0$-$C_4$ amine having one or two $C_1$-$C_8$ alkyl substituents, $C_0$-$C_4$ hydroxyl, $C_0$-$C_4$ carboxyl, $C_0$-$C_4$ sulfonate, and a quaternary amine or $$NH-\overset{R^4}{\underset{|}{CH}}-COR^7;$$

$R^5$ is H, or $$NH_2\overset{R^6}{\underset{|}{C^*H}}-\overset{O}{\underset{\|}{C}}-,$$

$R^6$ is an amino acid side chain of —H, —$NH_2$, —$C_{1-5}$ alkyl, —$C_{1-5}$ alkanol, —$C_{1-5}$ alkyl carboxylic acid, —$C_{1-5}$ alkyl amine, —$C_{1-5}$ alkyl amide, —$C_{1-5}$ alkyl imine, —$C_{1-5}$ alkyl delta-guanido and -methylphenyl; and $R^7$ is —O-isopropyl, —O-isobutyl, —O-tert-butyl, —O-isopentyl or —O-2-tert-pentyl; and C* is either a R- or S-chiral carbon atom. L is a nullity or a linker a group of $C_1$-$C_8$ alkyl, $C_1$-$C_8$ alkyl having a pendent heteroatom containing moiety of O, N or S present as a carboxyl, carbonyl, hydroxyl, amino, amido, sulfonyl, or quaternary amino. It is appreciated that a radioisotope or spectroscopically active label is readily added as a pendent moiety to the linker L.

Linker L is a nullity (no group at all) or optionally present between the chiral C* and the carbonyl carbon is operative as: a steric spacer facilitating enzymatic scission of the amino acid or other enzymatic activation steps, for attachment chemistry between the amino acid and the phosphonyl ester, to facilitate synthesis by pre-derivitizing the amino acid and the phosphonyl ester with the linker prior to conjugation, or to modify pharmacokinetics of the therapeutically active phosphonyl ester. The linker L is dictated by the required functionality. Conventional linker joining chemistries are hydrazide, ester, ether, and sulfhydryl. Amino caproic acid is an example of a bifunctional linker group L. An inventive prodrug in which n is one, L is a nullity, and $R^6$ is a naturally occurring amino acid side chain in every occurrence of either a C*, R- or S-chiral carbon represents a particularly efficacious orally bioavailable form. Further, $R^3$ being —$CH_2$—, $R^5$ being $$NH_2\overset{R^6}{\underset{|}{C^*H}}-\overset{O}{\underset{\|}{C}}-$$

and $R^8$ being $OR^9$ is still a more efficacious orally bioavailable form.

An inventive foscarnet prodrug has the formula:

$$\text{(VI)}$$

where $R^8$ in each occurrence is OH, $OR^9$, $$\overset{R^5}{\underset{|}{OCH_2C^*HCOOR^7}}, \text{ or } \overset{R^6}{\underset{|}{NHC^*HCOOR^7}};$$

$R^3$, $R^5$, $R^6$, $R^7$, $R^{10}$, L, n and Q are as described above with respect to Formula (I); and $R^9$ is a $C_1$-$C_5$ alkyl, —$(CH_2)_n$—$C_6R_5^{10}$, —$(CH_2)_n$—CH—$(C_6R_5^{10})_2$, —$(CH_2)_nC(C_6R_5^{10})_3$, or —$C_5N'R_5^{10}$; C* is either a R- or S-chiral carbon atom.

An inventive foscarnet prodrug in which n is zero, L is a nullity and $R^6$ is a naturally occurring amino acid side chain in every occurrence of either a C*, R- or S-chiral carbon represents a particularly efficacious orally bioavailable form. $R^3$ being —$CH_2$—, $R^5$ being

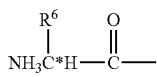

and R[8] being OR[9] is a still more efficacious orally bioavailable form of foscarnet.

DETAILED DESCRIPTION OF THE INVENTION

Figure 1:
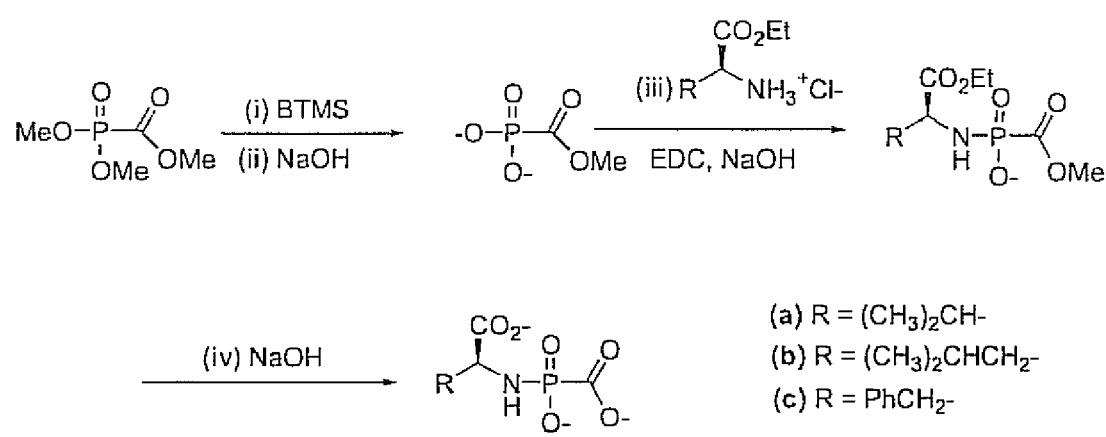
FIG. 1 shows the reaction scheme for synthesizing an amino acid linked to phosphonoformic acid.

The present invention has utility as prodrugs of therapeutic foscarnet and cidofovir to enhance oral bioavailability.

In the cidofovir-based compound of formula (III), each $R_1$ can be H, or an amino acid residue, a dipeptide, a tripeptide, or derivative thereof. The term "amino acid residue" means an amino acid lacking a portion of its structure. Examples include an amino acid without the OH portion of the α-carboxyl group, or lacking the H portion of the α-amino group. Also included within the definition of an amino acid residue is an amino acid lacking a portion of its side chain, such as a serine amino acid lacking the H portion of the side chain —OH group.

A derivative of an amino acid residue is an amino acid residue having a portion of its structure substituted by an atom or molecular group. Examples of such derivatives include, but are not limited to, ester derivatives having an —OR group substituting for the α-carboxyl-OH group, where R is an alkyl or alkenyl group. In preferred embodiments, R is a $C_1$-$C_{20}$ alkyl or alkenyl group. A dipeptide or tripeptide derivative is a peptide that contains at least one derivative of an amino acid residue.

An amino acid residue can be based on any one of the twenty common amino acids found in naturally synthesized proteins as long as the residue provides for the oral bioavailability of a cidofovir-based compound of the present invention. The residue can also be based on a modified or unusual amino acid. Examples of modified or unusual amino acids include, but are not limited to, 2-aminoadipic acid, 3-aminoadipic acid, β-alanine, 2-aminobutyric acid, piperidinic acid, 6-aminocaproic acid, 2-aminoheptanoic acid, 2-aminoisobutyric acid, 3-aminoisobutyric acid, 2-aminopimelic acid, 2,4-diaminobutyric acid, desmosine, 2,2'-diaminopimelic acid, 2,3-diaminopropionic acid, N-ethylglycine, N-ethylasparagine, hydroxylysine, allo-hydroxylysine, 3-hydroxyproline, 4-hydroxyproline, isodesmosine, isodesmosine, N-methylglycine, N-methylisoleucine, N-methylvaline, norvaline, norleucine, ornithine and homoserine.

Similarly, a dipeptide or tripeptide can contain any of the twenty common amino acids and any of the modified or unusual amino acids as long as the dipeptide and tripeptide support the oral bioavailability of the cidofovir-based compounds of the present invention.

Both the (D) and (L) stereoisomers of an amino acid residue can be incorporated into the cidofovir-based compounds. When the configuration is not designated, the amino acid or residue can have the configuration (D), (L) or (DL). For the purposes of this application, unless expressly noted to the contrary, a named amino acid shall be construed to include both the (D) or (L) stereoisomers. In preferred embodiments, when $R_1$ is an amino acid residue or a peptide, $R_1$ is prepared from L-amino acids.

In general, the incorporation of one or more amino acids into cidofovir or cyclic cidofovir leads to stereoisomeric forms of the cidofovir-based compounds. The present invention contemplates all such forms of the compounds, including cis- and trans-isomers, R- and S-enantiomers, diastereomers, (D)-isomers, (L)-isomers, the racemic mixtures thereof, and other mixtures thereof, as, falling within the scope of the invention. Additional asymmetric carbon atoms may be present in a substituent such as an alkyl group. All such isomers, as well as mixtures thereof, are intended to be included in this invention. Preferred embodiments are individual isomeric forms of the cidofovir-based compounds, which can be isolated for example by high performance liquid chromatography (HPLC).

The term "cidofovir framework" or "cyclic cidofovir framework" refers to the portion of cidofovir or cyclic cidofovir that remains following attachment of a chemical moiety that promotes uptake by a gastrointestinal membrane transporter or otherwise enhances oral bioavailability.

The term "cidofovir-based compound" refers to both cidofovir and cyclic cidofovir derived compounds.

In the compound of formula (II), $R_1$ can be attached to the cidofovir or cyclic cidofovir framework at N, O or P by an α-amino or side chain nitrogen, α-carboxyl carbon or side chain of $R_1$ when $R_1$ is an amino acid residue or a peptide. When $R_1$ is a peptide, the term "α-amino or side chain nitrogen, α-carboxyl carbon or side chain of $R_1$" refers to an α-amino or side chain nitrogen, α-carboxyl carbon or side chain of any amino acid residue of the peptide.

One way of preparing a compound having an amino acid or a peptide linked to a pentavalent phosphate group is shown by Marma, M. S. et al., Bioorganic & Medicinal Chemistry Letters 2004, 14, 1787-1790, herein incorporated by reference. As shown in this reference, an amino acid can be linked to the pentavalent phosphate group of phosphonoformic acid (foscarnet; PFA) by the 1-[3-(dimethylamino)propyl]-3-ethylcarbodiimide hydrochloride (EDC)-promoted coupling of a dianionic PFA C-monoester with a C-ethyl protected L-amino acid in aqueous solution under neutral to slightly alkaline conditions.

Figure 2:
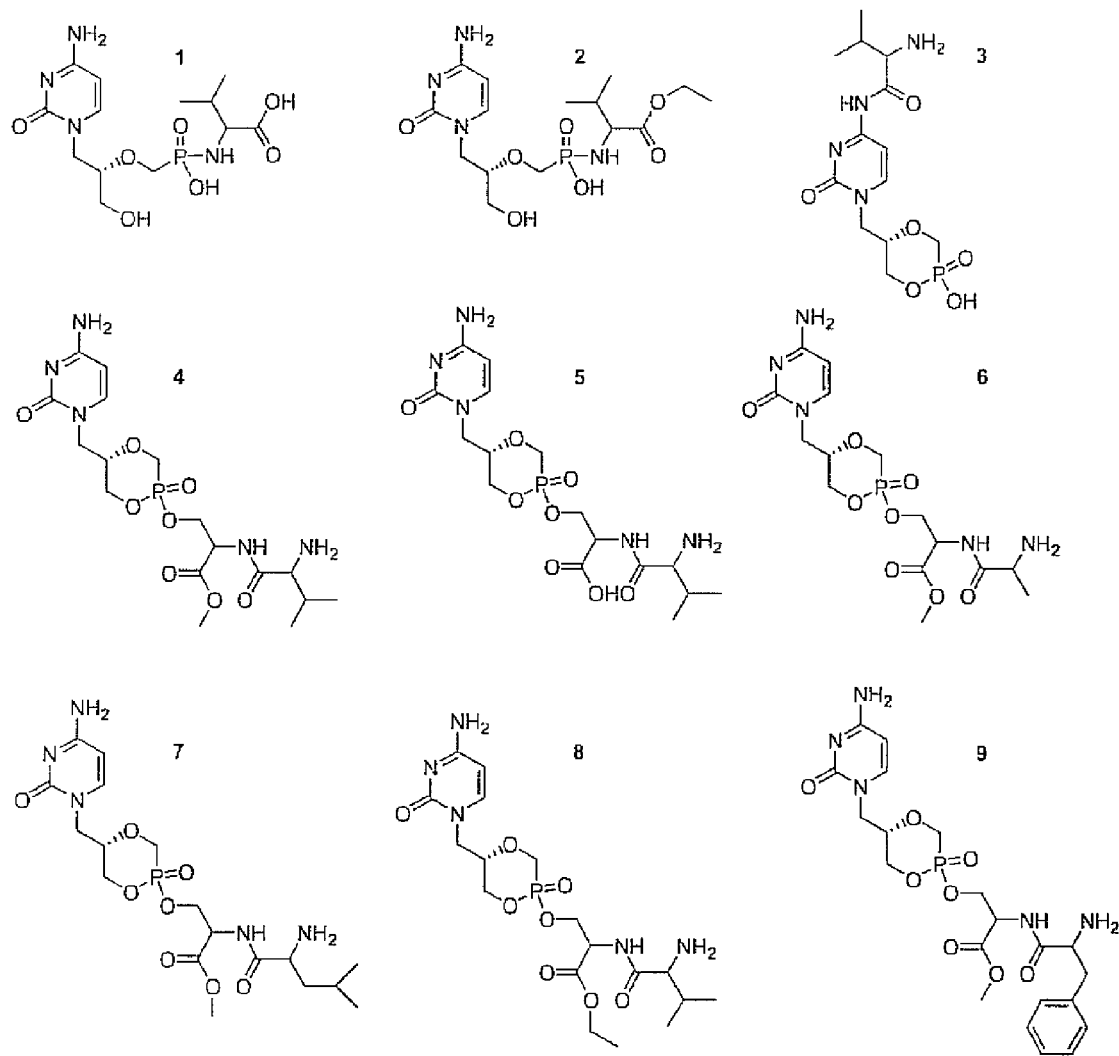
FIG. 2 shows the structures of various cidofovir-based compounds.

Exemplary embodiments of the present invention based on the compound of formula (III) are presented in FIG. 2. These examples show different types of bonding of $R_1$ to the cidofovir or cyclic cidofovir framework when $R_1$ is an amino acid residue or a peptide. In particular, structures 1 and 2 of FIG. 2 show a valine residue connected to P by an α-amino nitrogen, structure 3 shows a valine reside attached to N by an α-carboxyl carbon, and structures 4-9 show a serine residue connected to O by the serine side chain.

Another embodiment of the present invention is a cidofovir-based compound of formula (IV), where R is an amino acid residue, a dipeptide, a tripeptide, or a derivative thereof.

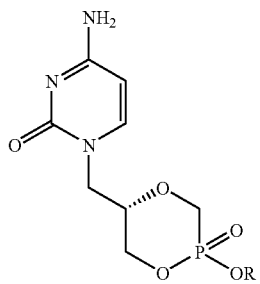

(IV)

In the compound of formula (IV), R is preferably connected to the cyclic cidofovir framework by the side chain of an L-serine, L-threonine or L-tyrosine residue, or a derivative thereof. In preferred embodiments, R is connected by the side chain of an L-serine residue or a derivative of an L-serine residue. Particularly preferred serine residue derivatives are ester derivatives having an OR group instead of an α-carboxyl-OH group, where R is a $C_1$-$C_{20}$ alkyl or alkenyl group. A serine derivative of this sort is designated herein as a Ser-$CO_2$—R ester. Structures 4, 6, 7 and 9 of FIG. 2 provide examples of Ser-$CO_2$-methyl ester derivatives, while structure S provides an example of a Ser-$CO_2$-ethyl ester derivative.

When R is a dipeptide, the serine residue is preferably the C-terminal residue. By convention, this dipeptide can be represented as X-Ser, where X is the N-terminal residue. In other embodiments, the dipeptide can be represented by Ser-X, where the serine residue is the N-terminal residue. Exemplary embodiments of dipeptides containing serine residues or serine residue derivatives are shown in structures 4-9 of FIG. 2. Although X can be any amino acid residue or amino acid residue derivative that provides for oral bioavailability, X preferably has a hydrophobic side chain. In particularly preferred embodiments, X is L-valine, L-leucine, L-alanine, L-phenylalanine, L-isoleucine, L-glycine, or a derivative of one of these residues. Preferably, X has a free amino terminus.

When R is a tripeptide, the peptide preferably has the sequence $X_1$-$X_2$-Ser or the sequence $X_1$-Ser-$X_2$, where $X_1$ and $X_2$ are each independently any amino acid residue or derivative that supports oral bioavailability. In other embodiments, the peptide can have the sequence Ser-$X_1$-$X_2$. As with dipeptides, $X_1$ and $X_2$ are preferably hydrophobic amino acids, with L-valine, L-leucine, L-alanine, L-phenylalanine, L-isoleucine, L-glycine, or a derivative of one of these residues being most preferred. In addition, the N-terminal residue $X_1$ preferably has a free amino terminus.

An inventive prodrug compound also has the formula;

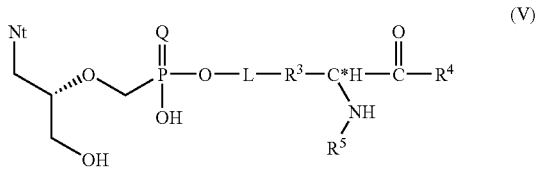

(V)

where Nt is

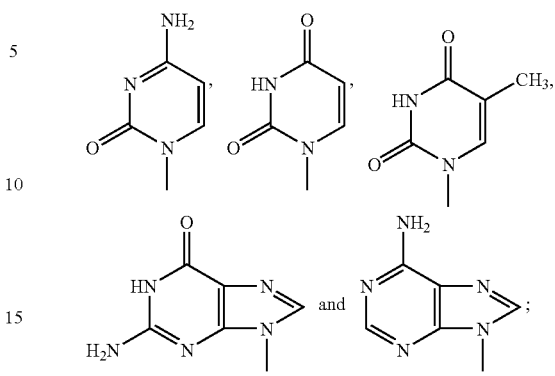

Q is O or S; $R^3$ is —$(CH_2)_n$—, —$CHCH_3(CH_2)_n$—, and —$(C_6H_4)(CH_2)_n$; $R^4$ is O-isopropyl, O-isobutyl, O-tert-butyl or O-2-tert-pentyl, —O—$(CH_2)_n$—$C_6R_5^{10}$, —O—$(CH_2)_n$—CH—$(C_6R_5^{10})_2$, —O—$(CH_2)_nC(C_6R_5^{10})_3$, and —O—$C_5N'R_5^{10}$; n is independently in each occurrence an integer between 0 and 12; $R^{10}$ is independently in each occurrence H, F, Cl, Br, $C_1$-$C_4$ alkyl, $C_0$-$C_4$ primary amine, $C_0$-$C_4$ amine having one or two $C_1$-$C_8$ alkyl substituents, $C_0$-$C_4$ hydroxyl, $C_0$-$C_4$ carboxyl, $C_0$-$C_4$ sulfonate, and a quaternary amine or

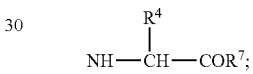

$R^5$ is H, or

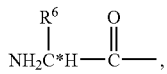

$R^6$ is an amino acid side chain of —H, —$NH_2$, —$C_{1-5}$ alkyl, —$C_{1-5}$ alkanol, —$C_{1-5}$ alkyl carboxylic acid, —$C_{1-5}$ alkyl amine, —$C_{1-5}$ alkyl amide, —$C_{1-5}$ s alkyl imine, —$C_{1-5}$ alkyl delta-guanido and -methylphenyl; and $R^7$ is —O-isopropyl, —O-isobutyl, —O-tert-butyl, —O-isopentyl or —O-2-tert-pentyl; and C* is either a R- or S-chiral carbon atom. L is a nullity or a linker a group of $C_1$-$C_8$ alkyl, $C_1$-$C_8$ alkyl having a pendent heteroatom containing moiety of O, N or S present as a carboxyl, carbonyl, hydroxyl, amino, amido, sulfonyl, or quaternary amino. It is appreciated that a radioisotope or spectroscopically active label is readily added as a pendent moiety to the linker L.

Linker L is a nullity (no group at all) or optionally present between the chiral C* and the carbonyl carbon is operative as: a steric spacer facilitating enzymatic scission of the amino acid or other enzymatic activation steps, for attachment chemistry between the amino acid and the phosphonyl ester, to facilitate synthesis by pre-derivitizing the amino acid and the phosphonyl ester with the linker prior to conjugation, or to modify pharmacokinetics of the therapeutically active phosphonyl ester. The linker L is dictated by the required functionality. Conventional linker joining chemistries are hydrazide, ester, ether, and sulfhydryl. Amino caproic acid is an example of a bifunctional linker group L. An inventive prodrug in which n is one, L is a nullity, and $R^6$ is a naturally occurring amino acid side chain in every occurrence of either a C*, R- or S-chiral carbon represents a particularly efficacious orally bioavailable form.

Further, $R^3$ being —CH$_2$—, $R^5$ being

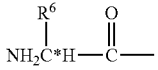

and $R^8$ being $OR^9$ is still a more efficacious orally bioavailable form.

An inventive foscarnet prodrug has the formula:

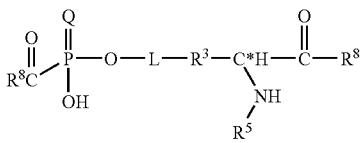
(VI)

where $R^8$ in each occurrence is OH, $OR^9$,

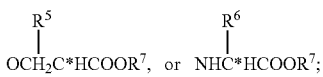

$R^3$, $R^5$, $R^6$, $R^7$, $R^{10}$, L, n and Q are as described above with respect to Formula (I); and $R^9$ is a $C_1$-$C_5$ alkyl, —(CH$_2$)$_n$—$C_6R_5^{10}$, —(CH$_2$)$_n$—CH—(C$_6$R$_5^{10}$)$_2$, —CH$_2$)$_n$C(C$_6$R$_5^{10}$)$_3$, or —C$_5$N'R$_5^{10}$; C* is either a R- or S-chiral carbon atom.

An inventive foscarnet prodrug in which n is zero, L is a nullity and R6 is a naturally occurring amino acid side chain in every occurrence of either a C*, R- or S-chiral carbon represents a particularly efficacious orally bioavailable form. $R^3$ being —CH$_2$—, $R^5$ being

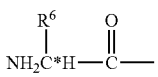

and $R^8$ being $OR^9$ is a still more efficacious orally bioavailable form of foscarnet.

An inventive prodrug compound is also provided of the formula:

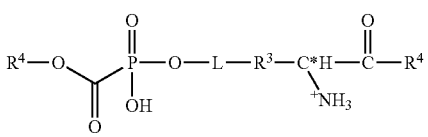
(VII)

where $R^3$ is —(CH$_2$)$_n$—, —CHCH$_3$(CH$_2$)$_n$, and —(C$_6$H$_4$)(CH$_2$)$_n$; $R^4$ is O-isopropyl, O-isobutyl, O-tert-butyl or O-2-tert-pentyl, —O—(CH$_2$)$_n$—C$_6$R$_5^{10}$, —O—(CH$_2$)$_n$—CH—(C$_6$R$_5^{10}$)$_2$, —O—(CH$_2$)$_n$C(C$_6$R$_5^{10}$)$_3$, and —O—C$_5$N'R$_5^{10}$; n is independently in each occurrence an integer between 0 and 12; $R^{10}$ is independently in each occurrence H, F, Cl, Br, $C_1$-$C_4$ alkyl, $C_0$-$C_4$ primary amine, $C_0$-$C_4$ amine having one or two $C_1$-$C_8$ alkyl substituents, $C_0$-$C_4$ hydroxyl, $C_0$-$C_4$ carboxyl, $C_0$-$C_4$ sulfonate, and a quaternary amine or

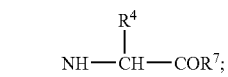

$R^5$ is H, or

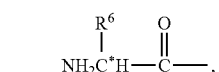

$R^6$ is an amino acid side chain of —H, —NH$_2$, —C$_{1-5}$ alkyl, —C$_{1-5}$ alkanol, —C$_{1-5}$ alkyl carboxylic acid, —C$_{1-5}$ alkyl amine, —C$_{1-5}$ alkyl amide, —C$_{1-5}$ alkyl imine, —C$_{1-5}$ alkyl delta-guanido and -methylphenyl; and $R^7$ is —O-isopropyl, —O-isobutyl, —O-tert-butyl, —O-isopentyl or —O-2-tert-pentyl; and C* is either a R- or S-chiral carbon atom. L is a nullity or a linker a group of $C_1$-$C_8$ alkyl, $C_1$-$C_8$ alkyl having a pendent heteroatom containing moiety of O, N or S present as a carboxyl, carbonyl, hydroxyl, amino, amido, sulfonyl, or quaternary amino. It is appreciated that a radioisotope or spectroscopically active label is readily added as a pendent moiety to the linker L.

The present invention also provides a pharmaceutical composition comprising a therapeutically effective amount of a cidofovir-based compound of the present invention, or a pharmaceutically acceptable salt thereof. A therapeutically effective amount is an amount that results in an improvement or a desired change in condition for which the cidofovir compound is administered, when the compound is administered once or over a period of time. For example, with respect to virus infections, the improvement can be a lowering of virus titer, or a reduction in the symptoms or discomfort associated with a viral infection. As is known, the amount will vary depending on such particulars as the type of virus infection, the condition being treated, the specific cidofovir compound utilized, the severity of the condition, and the characteristics of the patient.

Pharmaceutically acceptable salts are well known in the art and include salts prepared from pharmaceutically acceptable non-toxic acids, including inorganic acids and organic acids. Suitable non-toxic acids include inorganic and organic acids such as acetic, benzenesulfonic, benzoic, camphorsulfonic, citric, ethenesulfonic, fumaric, gluconic, glutanic, hydrobromic, hydrochloric, isethionic, lactic, maleic, malic, mandelic, methanesulfonic, mucic, nitric, pamoic, pantothenic, phosphoric, succinic, sulfuric, tartaric acid, p-toluenesulfonic, hydrochloric, hydrobromic, phosphoric, sulfuric acids, and the like. Salts formed with, for example, a free carboxy group of an amino acid residue or a peptide, can be derived from inorganic bases including, but not limited to, sodium, potassium, ammonium, calcium or ferric hydroxides, and organic bases including, but not limited to, isopropylamine, trimethylamine, histidine, and procaine.

A pharmaceutical composition of the present invention will typically contain a pharmaceutically acceptable carrier. Although oral administration of a cidofovir-based compound of the present invention is the preferred route of administration, other means of administration such as nasal, topical or rectal administration, or by injection or inhalation, are also contemplated. Depending on the intended mode of administration, the pharmaceutical compositions may be in the form of solid, semi-solid or liquid dosage forms, such as, for example, tablets, suppositories, pills, capsules, powders, liquids, suspensions, ointments or lotions, preferably in unit dosage form suitable for single administration of a precise dosage. The compositions can include an effective amount of the selected cidofovil-based compound in combination with a pharmaceutically acceptable carrier and, in addition, may include other pharmaceutical agents such as another antiviral agents, adjuvants, diluents, buffers, and the like. The compounds may thus be administered in dosage formulations containing conventional non-toxic pharmaceutically acceptable carriers, adjuvants and vehicles. The amount of active compound administered will be dependent on the subject being treated, the subject's weight, the manner of administration and the judgment of the prescribing physician.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the lice. Liquid pharmaceutically administrable compositions can, for example, be prepared by dissolving, dispersing, etc., an active compound as described herein and optional pharmaceutical adjuvants in an excipient, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan mono-laurate, triethanolamine sodium acetate, triethanolamine oleate, etc. Actual methods of preparing such dosage forms are known, or will be apparent, to those skilled in this art. For oral administration, the composition will generally take the form of a tablet or capsule, or may be an aqueous or nonaqueous solution, suspension or syrup. Tablets and capsules for oral use will generally include one or more commonly used carriers such as lactose and corn starch. Lubricating agents, such as magnesium stearate, are also typically added. When liquid suspensions are used, the active agent may be combined with emulsifying and suspending agents. If desired, flavoring, coloring and/or sweetening agents may be added as well. Other optional components for incorporation into an oral formulation herein include, but are not limited to, preservatives, suspending agents, thickening agents, and the like.

The present invention also provides a method of treating a virus infection, comprising administering to a virus-infected individual a therapeutically effective amount of a cidofovir-based compound of the present invention. The preferred route of administration is oral. Preferably, the virus infection is caused by a member of the polyomaviridae, papillomaviridae, adenoviridae, iridoviridae, hepadnaviridae, poxyiridae or herpesviridae families. More preferably, the virus infection is a smallpox virus infection, a cytomegalovirus infection, a hepatitis B virus or an adenovirus infection.

The present invention may be better understood by referring to the accompanying examples, which are intended for illustration purposes only and should not in any sense be construed as limiting the scope of the invention as defined in the claims appended hereto.

EXAMPLE 1

Synthesis of Cidofovir [(S)-1-(3-hydroxy-2-phosphonylmethoxypropyl)cytosine, HPMPC]

Figure 3:
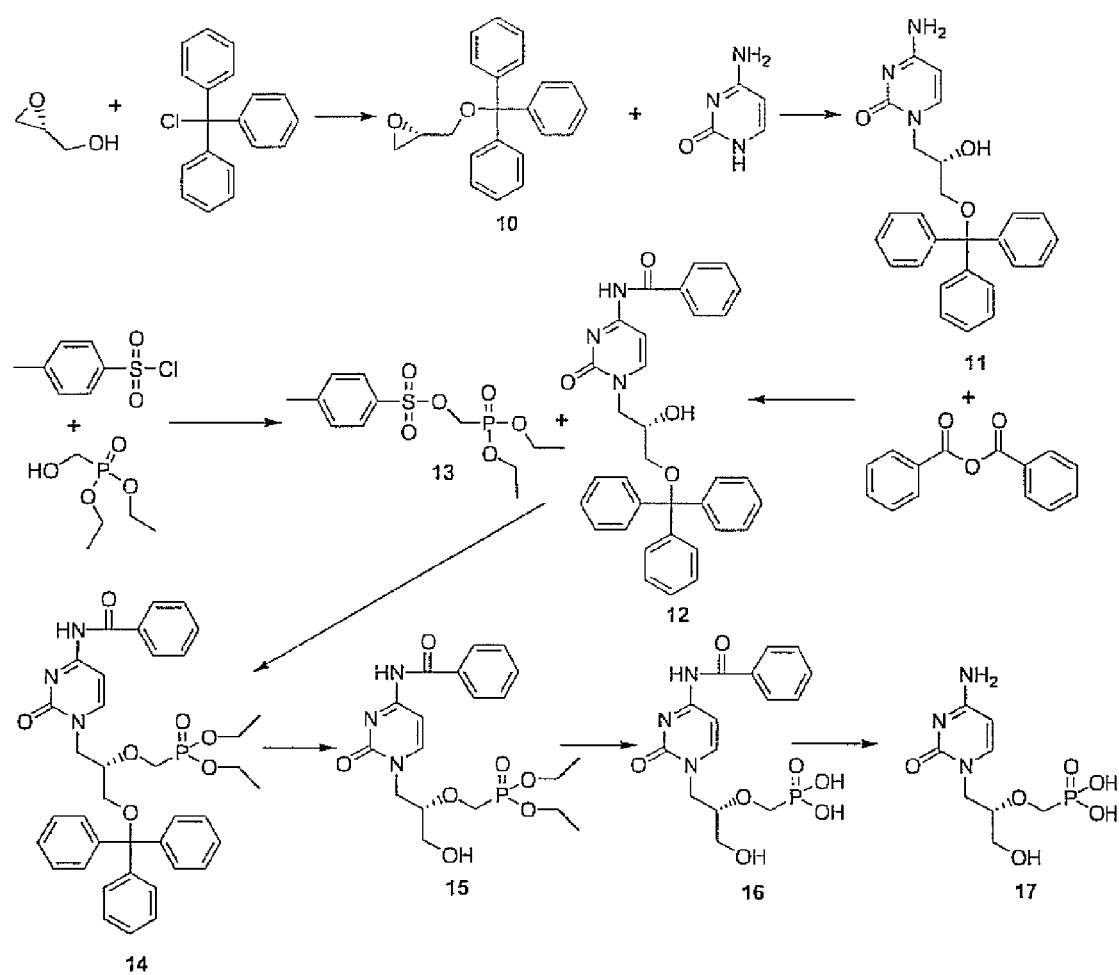
FIG. 3 shows the reaction scheme for synthesizing cidofovir.

A procedure from the literature for synthesizing cidofovir (P. R. Brodfuehrer, et al., Tetrahedron Lett. 35, 1994, 3243-3246, herein incorporated by reference) was modified. The modified synthesis reaction is shown in FIG. 3, The literature procedure of reacting tritylated R-glycidol and benzoyl protected cytosine produced low yields. Therefore, as shown in FIG. 3, tritylated R-glycidol (compound 10), (5.0 mmol) was treated with unprotected cytosine (5.0 mmol) in the presence of $K_2CO_3$ (5.0 mmol) in DMF (20 mL) for 5 h at 105° C. to obtain regiospecific opening of the epoxide, giving compound 11, (S)—$N^1$-[(2-hydroxy-3-triphenylmethoxy)propyl]cytosine). A benzoyl moiety was then introduced by reacting compound 11 (3.6 mmol) and benzoic anhydride (1.2 eq) in pyridine (15.5 mL) and DMF (8 mL) at 10° C. for 3 h to obtain the desired product, compound 12, (S)—$N^1$-[(3-triphenylmethoxy-2-hydroxy)propyl]-$N^4$-benzoylcytosine. The other steps of the synthesis were carried out as described by Brodfuehrer et al.

EXAMPLE 2

Synthesis of a Compound Having Valine Linked to the Phosphate Group of Cidofovir To prepare compound 1 of FIG. 2, 100 mg (0.32 mmol) of cidofovir, 303 mg (1.58 mmol) of 1-[3-(dimethylamino)propyl]-3-ethylcarbodiimide hydrochloride (EDC), and 266 mg (1.58 mmol) L-valine methyl ester hydrochloride were dissolved in 1.5 mL of HPLC grade water. The pH was adjusted to 7.4 using TEA, and the condensation reaction was carried out for 3 h at 40° C. 1.5 mL of ethyl acetate was added for extraction purposes before the hydrolysis of the methyl ester was carried out by adjusting the pH to 12 (by addition of NaOH). The hydrolysis reaction was carried out for 3 h at room temperature before purification of 1 was achieved by preparative HPLC using a C-18 column (5 μm, 100 Å, 21.4× 250 mm by Varian). The mobile phase contained 0.1 M triethylamine with 3% acetonitrile, carbonated to a pH of 7.4. A flow rate of 7 mL/min was used at ambient temperature, and an UV detector set at 254 nm and 208 nm was used to visualize the HPLC traces. The desired compound showed a retention time of 25 min in this system, and 1 was collected. The pH was adjusted to 9 using TEA and immediately frozen by immersion of the combined test tube fractions in a dry ice-acetone bath and was thereafter lyophilized to dryness. $^1$H NMR ($CD_3OD$): δ 0.80 (3H, d, J=6.8), 0.87 (3H, d, J=7.2), 1.80-1.92 (1H, m), 2.91-3.99 (8H, m), 5.75-5.77 (1H, d, J=7.6), 7.64-7.66 (1H, d, J=7.6). $^{31}$P NMR ($CD_3OD$): δ 17.27 (1P, s). Exact Mass ($C_{13}H_{22}N_4O_7P$): 377.1227 m/z. Yield: 37% by $^{31}$P NMR.

EXAMPLE 3

Synthesis of a Compound Having a Valine-$CO_2$-Alkyl Ester Linked to the Phosphate Group of Cidofovir To prepare compound 2, 100 mg (0.317 mol) of cidofovir, 204 mg (1.07 mmol) EDC, and 288 mg (1.59 mmol) L-valine-ethylester hydrochloride were dissolved in 1.5 mL HPLC water, and the pH was adjusted to 7.5 using TEA. The reaction was carried out stirring for 4 h at 40° C. The pH was adjusted to 9.5 using NaOH and 3×2 mL of ethyl acetate were added for extraction purposes. Preparative HPLC using a microsorb C-18 column (5μ, 100 Å pore size, 21.4×250 mm by Varian) was used for purification where the mobile phase contained 0.1 M triethylamine and 13% acetonitrile carbonated to a pH of 7.1 and kept at a temperature of 10° C. The flow rate was set at 9 mL/min and a retention time of approximately 19 min was obtained for compound 2, which was monitored by LV detection at 254 nm. 2 was collected and immediately frozen by immersion of the combined test tube fractions in a dry ice-acetone bath and was thereafter lyophilized to dryness. $^1$H NMR (CD$_3$OD): δ 0.84 (3H, d, J=7.0), 0.92 (3H, d, J=7.0), 1.14 (3H, t, J=7.0), 2.05 (1H, m), 3.26-4.11 (10H, m), 5.73 (1H, d, J=6.9), 7.60 (1H, d, J=6.9). $^{31}$P NMR (CD$_3$OD): δ 16.86 (1P, s). Exact Mass (C$_{15}$H$_{26}$N$_4$O$_7$P): 405.1555 m/z. Yield: 35% by $^{31}$P NMR.

EXAMPLE 4

Figure 5:
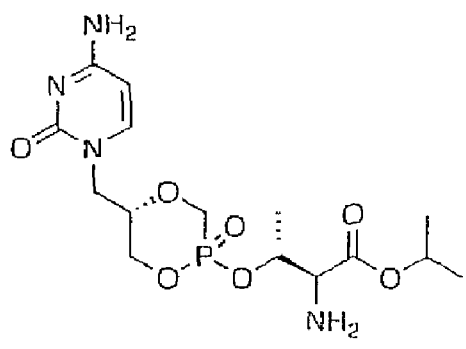
FIG. 5 shows the structures of various threonine esters of cyclic cidofovir.
Figure 5:
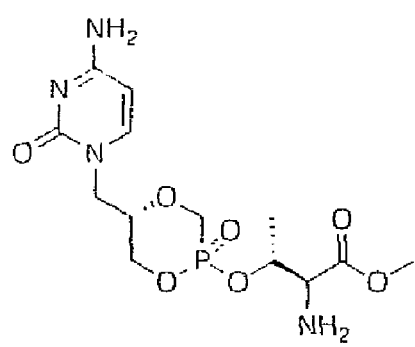

Synthesis of a Compound Having Valine Linked to the Cytosine Ring of Cidofovir cHPMPC-(N—C)-L-Valine-NH$_2$ (3). To prepare compound 3 of FIG. 5, 100 mg (0.32 mmol) cidofovir, 392 μL (2.25 mmol), diisopropylethylamine (DIEA), and 257 μL (6.35 mmol) methanol were mixed before 4 mL of dimethylformamide (DMF) was added to the reaction flask. 660 mg (1.26 mmol) PyBOP was added and the condensation reaction was carried out for 3 h at 35° C. Solvents were removed under vacuum and residues redissolved in 3 mL of DMF. 83 mg (0.38 mmol) of t-BOC-L-valine hydrochloride, 392 μL (2.25 mmol) DIEA, and 330 mg (0.63 mmol) PyBOP were added to the solution, and the reaction was carried out for 24 h at room temperature. Solvents were removed under vacuum followed by purification of the methyl protected 3 on a cyclograph (rotor: 4 mm) [eluent: (CH$_2$Cl$_2$), (CH$_2$Cl$_2$:acetone, 1:3) and (CH$_2$Cl$_2$: acetone, 1:1)]. The methyl-protected compound 3 was dissolved in 4 mL of DNT and 0.5 mL of BTMS was added. The demethylation reaction took place stirring for 16 h at room temperature. Solvent was removed under vacuum. Residues were redissolved in water followed by adjustment of the pH to 7 by addition of sodium carbonate. The solvent was evaporated under vacuum, and acetone was added to precipitate the desired compound. 160 mg of white crystals were obtained from the precipitation, and 3 was further purified by preparative HPLC using a C-18 column (5 μm, 100 Å, 21.4×250 mm by Varian). The mobile phase was kept at ambient temperature and contained 0.1 M triethylammonium carbonate and 7% acetonitrile with a pH of 7.4. A fraction of the sample was purified by preparative HPLC methods and further analyzed by NMR and HR-MS techniques. $^1$H$_1$ NMR (CD$_3$OD): δ 0.89 (6H, m), 2.01 (1H, m), 2.86-4.14 (7H, m), 4.35 (1H, d, J=8.2), 5.80 (1H, d, J=7.3), 7.35 (1H, d, J=7.3). $^{31}$P NMR (CD$_3$OD): δ 13.07. Exact Mass (C$_{13}$H$_{21}$N$_4$O$_6$P): 360.11987 m/z.

EXAMPLE 5

Synthesis of a Compound Having a Valine-Serine Dipeptide Linked to the Phosphate Group of Cyclic Cidofovir To synthesize compound 5 of FIG. 2, O-tert-butyl-N,N'-diisopropylisourea was made according to Rapoport et al., J. Org. Chem., 1993, 58, 2369-2376, incorporated by reference herein. In brief, 10 mL (1.0 equiv) of N,N'-diisopropylcarbodiimide was added to 7.1 mL (1.15 equiv) of t-butanol. 64 mg of CuCl was added and the reaction was stirred at ambient temperature for 24 h. 1.73 mL (7.25 mmol) O-tert-butyl-N, N'-diisopropylisourea was added to 1.0 g (4.87 mmol) of t-BOC-L-serine in 10.0 mL dry CH$_2$Cl$_2$. The reaction was refluxed for 24 h before an additional 1.73 mL (7.25 mmol) O-tert-butyl-N,N'-diisopropylisourea was added to the reaction mixture, which was refluxed for another 24 h. Solvents were removed under vacuum, and residues were redissolved in CH$_2$Cl$_2$, which was followed by a silica gel filtration for removal of N,N'-diiospropylurea. The filtrate solvent was removed and approximately 1.0 g of the t-butyl ester of t-BOC L-serine was achieved (yield 79%). Selective deprotection of the t-BOC moiety was achieved according to Han et al., J. Pept. Res. 2001, 58(4), 338-341, incorporated by reference herein, by exposing the t-butyl ester and t-BOC-protected L-serine to 4 M HCl in dioxane at 0° C. for 0.5 h. Solvent was removed under vacuum, and 751 mg of t-butyl ester-protected L-serine was obtained as a white crystalline compound. 751 mg (3.8 mmol) L-serine t-butylester, 826 mg (3.8 mmol) t-BOC L-valine, and 425 μL (3.05 mmol) TEA were dissolved in 15.0 mL dry CH$_2$Cl$_2$ to achieve the desired conjugation between the two amino acids, 695 mg (3.37 mmol) DCC and 434 mg (3.21 mmol) HOBt, was added, and the reaction was stirred at room temperature for 18 h. N,N'-dicyclohexylurea was filtered off and the crude product was concentrated under vacuum. The crude product was dissolved in 50 mL of DCM. An aqueous workup was performed using 25 mL sat. NaHCO$_3$ followed by 30 mL HPLC water before obtaining the desired dipeptide as a foamy film in 48% yield (650 mg). This product was used as obtained without further purification.

To prepare compound 5 of FIG. 2, 135 mg (0.428 mmol) cidofovir was exposed to 135 mg (1.04 mmol) DIEA and dissolved in 4 mL DMF. A HPMPC-DEEA salt was obtained after solvent was removed under vacuum. 650 mg (1.8 mmol) dipeptide (t-BOC-Val-Ser-t-butyl described above) was added to a reaction flask containing the HPMPC-DIEA salt and 4 mL dry DMF. 660 mg (1.27 mmol) PyBOP and 425 μL (2.44 mmol) DIEA were added, and the reaction took place stirring under N$_2$ (g) at 40° C. for 1 h. An additional 330 mg (0.635 mmol) PyBOP was added and left for 3 additional hours. Solvents were removed under vacuum, and a silica gel column chromatography purification was performed [eluent; CH$_2$Cl$_2$: acetone:methanol, 20:10:1.]. Solvent was removed and deprotection of the t-BOC and t-butoxy groups was performed in 4 mL of CH$_2$Cl$_2$ in the presence of 2 mL of 99% TFA for 3 h at room temperature. Solvents were removed under vacuum and ether was added to precipitate the final compound, 5, which was filtered by methanol on a funnel containing a silica gel layer. Preparative HPLC purification on a C-18 column (5 μm, 100 Å 21.4×250 mm by Varian) was obtained using a mobile phase containing 0.1 M TEA and 3.5% acetonitrile at pH 6.7 adjusted with acetic acid. A fraction of the sample was purified by preparative HPLC methods and evaluated by NMR and HR-MS techniques. $^1$H NMR (CD$_3$OD): δ 0.94 (6H, m), 2.10 (1H, m), 2.94-5.73 (10H, m), 5.73 (1H, m), 7.40 (1H, m). $^{31}$P NMR (CD$_3$OD): δ 14.3 and 15.6 (1P, 2s). Exact mass (C$_{16}$H$_{26}$N$_5$O$_8$P); 447.1519 m/z.

EXAMPLE 6

General Dipeptide Synthesis of L-Amino Acid-tBOC-L-Serine(OMe)

The method of synthesizing dipeptide-tBOC reagents was adopted with slight modifications from the literature (Maruyama, K. et al., J. Org. Chem., Vol. 57, No. 23, 1992, p6147, incorporated by reference herein). 500 mg (3.21 mmol) of L-methyl ester or ethyl ester of serine and the appropriate t-BOC protected amino acid (3.21 mmol) were reacted with 1.2 times excess of DCC in 20 mL of dry CH$_2$Cl$_2$ in the presence of 425 μL of TEA and HOBt (3.21 mmol). The reaction was stirred and carried out at room temperature for 16 h. The produced urea was filtered away, and solvent removed. Residues were re-dissolved in 50 mL of CH$_2$Cl$_2$ and washed with 25 mL of 0.5M citric acid followed by 25 mL of H$_2$O, as well as 25 mL of a sat. solution of NaHCO$_3$. The organic phase was dried over Na$_2$SO$_4$. Solvent was removed under vacuo and the residue redissolved in 25 mL CH$_2$Cl$_2$ and 25 mL of ethyl ether. The produced urea was filtered away after 16 h and solvents removed under vacuo. The white to yellow crystalline dipeptides were obtained in yields varying between 44-88%.

EXAMPLE 7

General Procedure for Cidofovir Condensation of L-Amino Acid-tBOC-L-Ser(OMe alt OEt)

5 mL of DMF and 400 µL of DIEA was added to 200 mg (0.63 mmol) HPMPC to produce a HPMPC-DIEA salt. Solvent was removed under vacuo and HPMPC-DIEA salt was carefully dried. 1.5 times excess of desired dipeptide from the general procedure described above was added to the dry HPMPC-DIEA salt, as well as 7 mL dry DMF and 400 µL DIEA. The mixture was heated for 1 h at 40° C. before 660 mg (1.3 mmol) PyBOP was added. Reaction was monitored by $^{31}$P NMR, and additional portions of PyBOP were added until the reaction was completed. Solvent was removed under vacuo, and purified by silica gel column chromatography [Solvent system: $(CH_2Cl_2)$, $(CH_2Cl_2$: acetone, 2:1), $(CH_2Cl_2$: acetone: MeOH, 20:10:3)].

EXAMPLE 8

General t-BOC Deprotection and Purification of Compounds 4, 6, 7, 8 and 9 of FIG. 2 t-BOC deprotection was achieved by exposing the compounds to TFA (2 mL of 99% TFA) in $CH_2Cl_2$ (4 mL) for 3 h at room temperature. The solvent was removed under vacuo and the product purified on a preparative TLC [$(CH_2Cl_2$: MeOH, 10:2), 1000 µm silica GF60 plate]. The product was extracted with methanol and dried under vacuo. A tiny amount (~200 µL) of MeOH was used to wet the film produced from drying and diethylether was added to precipitate the compounds. White crystals of compounds 4, 6, 7, 8 and 9 were obtained in yields ranging between 9-30%, which were not optimized.

4: cHPMPC-Val-Ser(OMe). $^1$H NMR (CD$_3$OD): δ 0.92-1.04 (6H, m), 2.06-2.20 (1H, m), 3.66 and 3.69 (3H, 2s), 3.71-4.50 (9H, m), 5.78-5.86 (1H, m), 7.50-7.60 (1H, 2d, J=7.7). 31P NMR (CD$_3$OD): a 14.1 and 15.3 (1P, 2s). MS: $C_{17}H_{29}N_5O_8P^+$; 462.175 m/z (M+H$^+$).

6: cHPMPC-Ala-Ser(OMe). $^1$H NMR (CD$_3$OD): δ 1.41-1.45 (3H, m), 3.66 and 3.69 (3H, 2s), 3.72-4.46 (9H, m), 5.83-5.87 (1H, m), 7.56-7.65 (1H, 2d, J=7.2). $^{31}$P NMR (CD$_3$OD): δ 14.0 and 15.2 (1P, 2s). MS: $C_{15}H_{25}N_5O_8P^+$; 434.145 m/z (M+H$^+$). Elem. Anal. ($C_{15}H_{24}N_5O_8P$): C, H; N: calcd, 34.50, 3.96, 10.59; found, 34.21, 4.17, 10.38.

7: cHPMPC-Leu-Ser(OMe). $^1$H NMR (CD$_3$OD): δ 0.89-0.94 (6H, m), 1.55-1.72 (3H, m), 3.67 and 3.69 (3H, 2s), 3.7-4.51 (11H, m), 5.79-5.83 (1H, m), 7.48-7.56 (1H, m). $^{31}$P NMR (CD$_3$OD): δ 14.14 and 15.24 (1P, 2s). MS: $C_{18}H_{31}N_5O_8P^+$; 476.192 m/z (M+H$^+$).

8: cHPMPC-Val-Ser(OEt). $^1$H NMR (CD$_3$OD): δ 1.00 (6H, m), 1.20 (3H, m), 2.14 (1H, m), 3.68-4.54 (13H, m), 5.85 (1H, m), 7.55 (2d, J=7.4). $^{31}$P NMR (CD$_3$OD): δ 14.92 and 13.88 (1P, 2s). MS: $C_{18}H_{31}N_5O_8P^+$; 476.189 m/z (M+H$^+$).

9: cHPMPC-Phe-Ser(OMe). $^1$H NMR (CD$_3$OD): δ 2.89-4.51 (13H, m), 3.66 and 3.68 (3H, 2s), 5.79-5.86 (1H, m), 7.15-7.30 (5H, m), 7.48-7.56 (1H, 2d, J=7.1). $^{31}$P NMR (CD$_3$OD): δ 14.04 and 15.28 (1P, 2s). MS: $C_{21}H_{29}N_5O_8P^+$; 510.178 m/z (M+H$^+$).

The cyclic cidofovir-based compounds are synthesized as diastereoisomers, which can be separated into individual isomers by HPLC.

EXAMPLE 9

Single Pass Perfusion and Portal Vein Blood Collection Analysis of Compounds

Male albino Sprague-Dawley rats, 9-10 weeks old and weighing 250-400 g were used in the study. Prior to each experiment, the rats were fasted for 18 h with free access to water. The rats were anesthetized with an i.m. injection of ketamine/xylazinelbutorphanol (87, 6, and 0.2 mg/kg body weight, respectively). The abdomen was opened by a midline incision of 4-5 cm. A suitable intestinal segment of approximately 10-20 cm was cannulated on two ends and connected to a syringe pump that guided the solution through a water bath of 37° C. This isolated segment was then rinsed with buffer at the respective pH at a flow-rate of 0.5 ml/min in order to clean out any residual debris. A 10 mM HEPES (pH 7.5) buffer containing 135 mM NaCl, 5 mM KCl and 0.01% PEG 4000 was used for the perfusion buffer. The intestinal segments were perfused at a flow rate of approximately 0.2 m/min with these buffers containing test drug and $^{14}$C-PEG 4000 as a non-absorbable marker for measuring water flux. After steady-state was reached in the segment, typically 30 min after the start of perfusion, perfusate samples were taken in 10 min intervals for an hour. Sample analysis for $^{14}$C (PEG-4000) was performed by scintillation counting. For these studies, we also took blood from the portal vein (prehepatic) as described below. After a segment of intestine was cannulated, the portal vein was then immediately cannulated using a 24-gauge Angeocath catheter (Becton Dickinson, Sandy, Utah). The cannula was secured in place using cyanoacrylate glue or surgical tape and connected to an approximately 35 cm long Silastic tubing, which allowed blood to flow into vials placed about 25 cm below the mesenteric vein. The single-pass intestinal perfusion was initiated at this time. Blood flowing out of the mesenteric vein from the isolated intestinal segment was collected directly into vials, centrifuged immediately and plasma was separated and stored at −80° C.

Rat plasma samples were acidified and processed with solid phase extraction. Briefly, a cation exchange solid-phase cartridge (MCX, 30 mg/i. cc, Waters) was activated with 1.0 ml of methanol and equilibrated with 1.0 ml of water. A 500 µl aliquot of rat plasma was acidified and loaded onto the cartridge. After washing with 1.0 ml of 0.1 N HCl and 1.0 ml methanol, the compounds were eluted with 1 ml of 5% NH$_4$OH in methanol. The solvent was evaporated under vacuum and the residue was reconstituted in 200 µl of water. Samples were analyzed using a LC-MS/MS system (Micromass Quattro II, HP 1100). Ten µl of sample was separated with a Cs column (2.1×150 mm) using a mobile phase of 5-10% acetonitrile:water containing 0.5% formic acid.

From the plasma concentration of compound, the mesenteric permeability was determined by substitution into Eq. (1), $$\text{Flux} = (A)(P_{e\text{-}mes})(C_i) \qquad \text{Eq. (1)}$$

where Flux is equal to the portal blood flow (estimated at 1 ml/min in the rat) X the steady state mesenteric blood concentration of cidofovir-based compound, A is the absorptive area of the intestine (estimated at 12.56 cm$^2$ in the rat intestine), Pe-mes is the mesenteric permeability (cm/s), and Ci is the starting concentration of the drug in the perfusate (1 g/ml).

The transport evaluations of compounds 4, 6 and 7 of FIG. 2 versus cidofovir and cyclic cidofovir in the single pass intestinal perfusion with portal vein collection assay showed about a 10-20 fold increase in permeability for compounds 4, 6 and 7 relative to cidofovir and cyclic cidofovir. Compound 4 was also co-perfused with glycine-sarcosine (Gly-Sar), a known competitive substrate of hPepT1 in the in situ perfusion model. Co-perfusion with Gly-Sar almost completely suppressed the transport of compound 4, indicating that hPepT1 is involved in the transportation of the cidofovir-based compounds of the present invention. The results are shown in Table I.

TABLE I

| COMPOUND | Pe-mes (cm/s × $10^5$) |
| --- | --- |
| Cidofovir | 0.052 |
| Cyclic cidofovir | 0.003 |
| Compound 4 | 1.18 |
| Compound 4 + Gly-Sar | 0.006 |
| Compound 6 | 0.98 |
| Compound 7 | 0.48 |

EXAMPLE 10

Competitive Binding Studies

Ki values for the cidofovir compounds were determined in the hPepT1 over-expressing cell line (DC5) using $^3$H glycine-sarcosine (Gly-Sar). DC5 cells were plated (12,000 cells/well) in 96-well tissue culture plates (Falcon) and allowed to grow for 4 days. The cells were washed once with 200 µl of uptake buffer and aspirated. The plates were cooled to 4° C. and 25 µl of uptake buffer containing 50 µM Gly-Sar (0.5 µCi/ml) was added. The uptake buffer also contained the test cidofovir-based compounds over a range of concentrations. Uptake was initiated by placing the plate in a shaker water bath (37° C.) and terminated at 10 min by rapid washing with multiple changes of 4° C. PBS (Sigma). The radioactive peptide was extracted from the cell layer with 200 µl of methanol:water (1:1) and counted in 4 ml of CytoScint ESTM scintillation cocktail (ICN). Non-linear regression analysis of the data was used to determine the $IC_{50}$ using the solver function in Microsoft Excel.

The competitive binding assay in DC5 cells over-expressing hPepT1 showed that compounds 4, 6 and 7 have significant affinity for PepT1. The results are shown in Table 2.

TABLE 2

| COMPOUND | Gly-Sar inhibition (mM), Ki |
| --- | --- |
| Cidofovir | 10.8 ± 0.3 |
| Cyclic cidofovir | 10.7 ± 0.2 |
| Compound 4 | 2.7 ± 0.1 |
| Compound 6 | 3.4 ± 0.2 |
| Compound 7 | 5.4 ± 0.2 |

The results of the perfusion and binding studies indicate that incorporating amino acid moieties into cidofovir and cyclic cidofovir enhances oral bioavailability and binding to the PepT1 transporter.

EXAMPLE 11

Dipeptidyl Isopropyl Esters of cHPMPC and HPMPC

Figure 4:
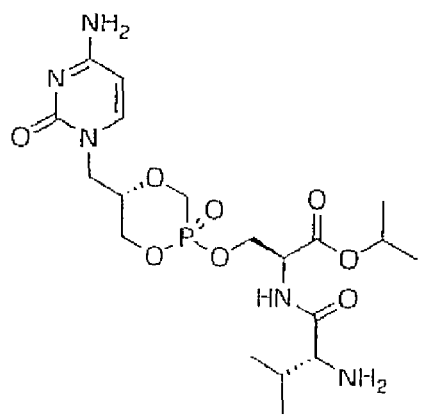
FIG. 4 shows the structures of various valine-serine isopropyl esters of cidofovir.
Figure 4:
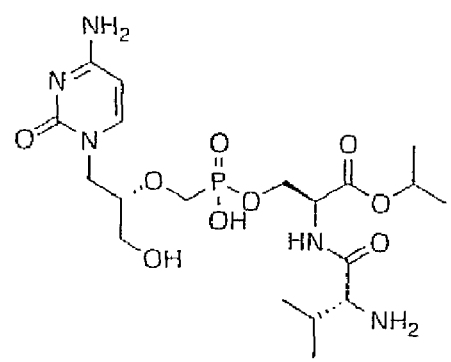
Figure 4:
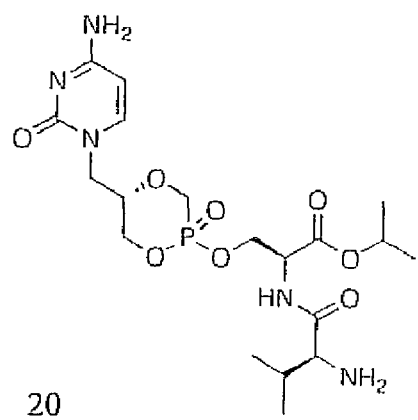
Figure 4:
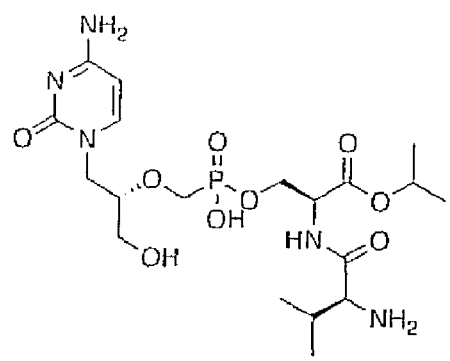

Cidofovir (HPMPC, I) and its equivalently potent cyclic form (cHPMPC, II) are active against orthopox virus infections, but are limited in this role by low oral bioavailability. In contrast to some alternative promoieties, peptides offer low toxicity together with versatility in tuning transport and activation pharmacology. The synthesis and biological evaluation of several prodrugs of cyclic cidofovir in which the phosphonic acid group was esterified by the free serine side-chain hydroxyl group of an X-Ser-$CO_2$ Me dipeptide are provided in the preceding examples. Val-Ser-$CO_2$Me cHPMPC (4) was stable at pH 3-5, but rapidly released the active drug in cell and tissue homogenates, while exhibiting enhanced transport vs. the parent drug in a rat model. Incorporation of D-amino acids, especially at the N-terminus, resulted in increased stability and improved transport, consistent with our present finding that co-dosing with the aminopeptidase inhibitor, bestatin, results in enhanced transport of 4. Seeking an optimal balance of transport and efficient activation, Val-Ser-$CO_2$iPr cHPMPC (18) was synthesized and was also found to be a useful synthon for preparation of its acyclic analog, Val-Ser-$Co_2$iPr HPMPC (19), as shown in FIG. 4. These syntheses were conducted as detailed above with the exception that the isopropyl (iPr) esters were used in place of methyl (Me) esters. Only L-amino acid dipeptide analogs of 18 and 19 were similarly synthesized and shown in FIG. 4 as structures 20 and 21, respectively. $^1$H and $^{31}$P NMR characterization of these compounds was consistent with the structures of FIG. 4, LC and LC-MS analysis of 4, 18 and 19 stability in buffer and in cell and tissue homogenates provides evidence that the activation efficiency and pathway are strongly dependent on the ester structure. The results further demonstrate the potential of this peptidization approach in the development of an orally effective form of cidofovir.

EXAMPLE 12

Threonyl Esters of CHPMPC

L-Thr-OiPr cHPMPC (22) and L-Thr-OMe cHPMPC (23) were synthesized according to the procedures of Examples 6-8 with the equimolar substitution of t-Boc-L-threonine salt (Thr) for t-Boc-dipeptide. H NMR characterization of these compounds was consistent with the structures of FIG. 5.

EXAMPLE 13

Esters of Foscarnet

Figure 6:
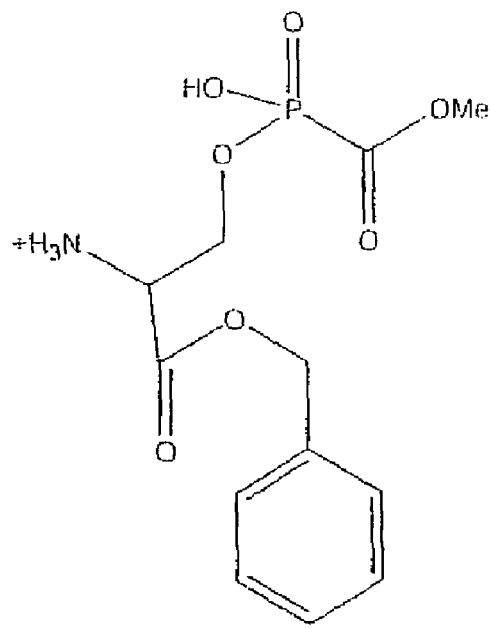
FIG. 6 shows the structures of various esters of foscarnet.
Figure 6:
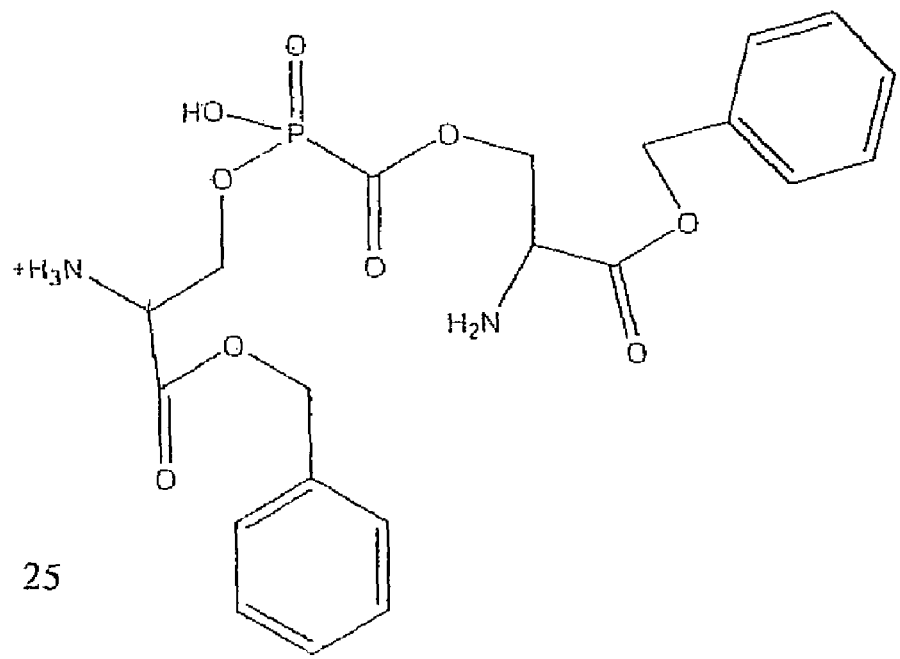

The specific compounds of VII, 24 and 25 as shown in FIG. 6, were synthesized with appropriate reagent substitutions relative to the above description, specifically with foscarnet in place of a cidofovir.

EXAMPLE 14

Two new approaches (UV detection via formation of a $Yb^{3+}$/pyrocatechol violet complex, and fluorescence detection by formation of a 9,10-bis[2,2'-dipicolylamino)methyl] anthracene zinc complex) show improved detection relative to conventional detection using liquid chromatography-mass spectrometry-mass spectrometry (LC-MS/MS).

Patent documents and publications mentioned in the specification are indicative of the levels of those skilled in the art to which the invention pertains. These documents and publications are incorporated herein by reference to the same extent as if each individual document or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

The invention claimed is:

1. A prodrug compound

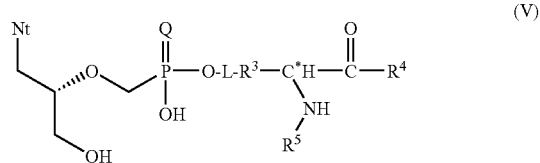

(V)

where Nt is

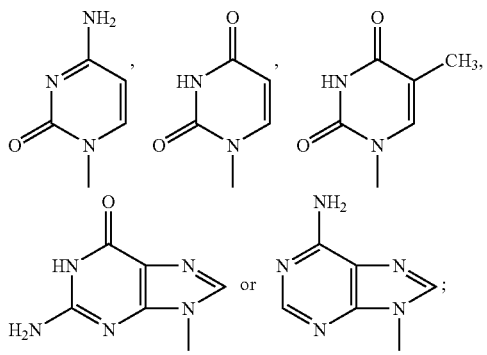

Q is O or S; $R^3$ is —$(CH_2)_n$—, —$CHCH_3(CH_2)_n$—, or —$(C_6H_4)(CH_2)_n$—; $R^4$ is O-isopropyl, O-isobutyl, O-tert-butyl, O-2-tert-pentyl, —O—$(CH_2)_n$—$C_6R_5^{10}$, —O—$(CH_2)_n$—CH—$(C_6R_5^{10})_2$, —O—$(CH_2)_nC(C_6R_5^{10})_3$, or —O—$C_5N'R_5^{10}$; n is independently in each occurrence an integer between 0 and 12; $R^{10}$ is independently in each occurrence H, F, Cl, Br, $C_1$-$C_4$ alkyl, $C_0$-$C_4$ primary amine, $C_0$-$C_4$ amine having one or two $C_1$-$C_8$ alkyl substituents, $C_0$-$C_4$ hydroxyl, $C_0$-$C_4$ carboxyl, $C_0$-$C_4$ sulfonate, and a quaternary amine or

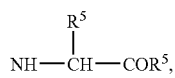

$R^5$ is H, or

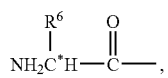

$R^6$ is an amino acid side chain of —H, —$NH_2$, —$C_{1-5}$ alkyl, —$C_{1-5}$ alkanol, —$C_{1-5}$ alkyl carboxylic acid, —$C_{1-5}$ alkyl amine, —$C_{1-5}$ alkyl amide, —$C_{1-5}$ alkyl imine, —$C_{1-5}$ alkyl delta-guanido and -methylphenyl; and $R^7$ is —O-isopropyl, —O-isobutyl, —O-tert-butyl, —O-isopentyl or —O-2-tert-pentyl; C* is either a R- or S-chiral carbon atom; and L is a nullity or a linker a group of $C_1$-$C_8$ alkyl, $C_1$-$C_8$ alkyl having a pendent heteroatom containing moiety of O, N or S present as a carboxyl, carbonyl, hydroxyl, amino, amido, sulfonyl, or quaternary amino.

2. A prodrug compound

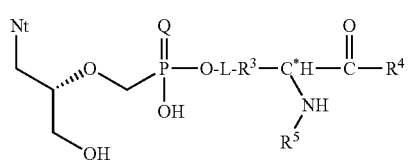

where Nt is

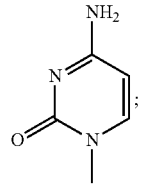

Q is O or S; $R^3$ is —$CH_2$—, $R^4$ is O-isopropyl; $R^5$ is

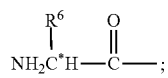

$R^6$ is —$CH(CH_3)_2$; L is a nullity; n is independently in each occurrence an integer between 0 and 12; $R^{10}$ is independently in each occurrence H, F, Cl, Br, $C_1$-$C_4$ alkyl, $C_0$-$C_4$ primary amine, $C_0$-$C_4$ amine having one or two $C_1$-$C_8$ alkyl substituents, $C_0$-$C_4$ hydroxyl, $C_0$-$C_4$ carboxyl, $C_0$-$C_4$ sulfonate, and a quaternary amine or

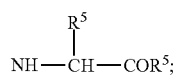

$R^5$ is H, or

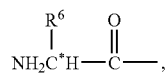

$R^6$ is an amino acid side chain of —H, —$NH_2$, —$C_{1-5}$ alkyl, —$C_{1-5}$ alkanol, —$C_{1-5}$ alkyl carboxylic acid, —$C_{1-5}$ alkyl amine, —$C_{1-5}$ alkyl amide, —$C_{1-5}$ alkyl imine, —$C_{1-5}$ alkyl delta-guanido and -methylphenyl; and $R^7$ is —O-isopropyl, —O-isobutyl, —O-tert-butyl, —O-isopentyl or —O-2-tert-pentyl; C* is either a R- or S-chiral carbon atom.

3. The compound of claim 2 wherein C* is a R-chiral carbon atom.

4. The compound of claim 1 wherein Nt is

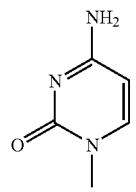

and $R^4$ is —O—$CH_2$—$C_6H_5$ or —O—$(CH_2)$—$C_6H_4R^{10}$ with the proviso $R^{10}$ is not H.

5. A cidofovir compound having the structure of various valine-serine isopropyl esters of cidofovir and various threonine esters of cyclic cidofovir.

* * * * *

UNITED STATES PATENT AND TRADEMARK OFFICE
CERTIFICATE OF CORRECTION

| | | |
|---|---|---|
| PATENT NO. | : 8,063,209 B2 | Page 1 of 1 |
| APPLICATION NO. | : 12/404764 | |
| DATED | : November 22, 2011 | |
| INVENTOR(S) | : John Hilfinger et al. | |

It is certified that error appears in the above-identified patent and that said Letters Patent is hereby corrected as shown below:

Column 6, Line 35, Delete "II" Insert --III--

Column 7, Line 29, After structure Delete "S" Insert --8--

Column 8, Line 43, Delete "$C_{1-5}$ s alkyl" Insert --$C_{1-5}$ alkyl--

Column 10, Line 46, Delete "glutanic" Insert --glutamic--

Column 11, Line 17, Delete "lice" Insert --like--

Column 13, Line 27, Delete "DNT" Insert --DMF--

Column 16, Line 3, Delete "ketamine/xylazinelbutorphanol" Insert --Ketamine/xylazine/butorphanol--

Column 16, Line 43, Delete "$C_s$" Insert --$C_8$--

Signed and Sealed this
Twenty-eighth Day of August, 2012

David J. Kappos
*Director of the United States Patent and Trademark Office*